United States Patent [19]

Shoesmith, deceased

[11] Patent Number: Plant 5,971

[45] Date of Patent: May 5, 1987

[54] CHRYSANTHEMUM PLANT NAMED FLARE

[75] Inventor: Leonard H. Shoesmith, deceased, late of Westfield, England, by May V. Shoesmith, executrix

[73] Assignee: Ball Pan Am Plant Company, Parrish, Fla.

[21] Appl. No.: 712,694

[22] Filed: Mar. 18, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Chrysanthemum named Flare having a dwarf habit, flat capitulum form and a single capitulum type, bronze-gold ray florets, eight week response, and an ability to be grown year around in 9 cm. pots with little growth regulation.

1 Drawing Figure

The present invention comprises a new and distinct cultivar of *Chrysanthemum morifolium,* Ramat., hereinafter referred to by the cultivar name Flare.

Flare is a product of a planned breeding program which had the objective of creating new Chrysanthemum cultivars with eight (8) week response, yellow daisy type flowers, and dwarf habit for year around growing in 9 cm. pots. Such traits in combination were not present in previously available commercial cultivars.

Flare was origniated from a hybridization made by Leonard H. Shoesmith in a controlled breeding program in Westfield, Woking, England in 1976. The male and female parents are unknown at this time. Flare was discovered and selected as one flowering plant within the progeny of the parentage by applicant in November, 1977 in a controlled environment in West Chicago, Ill., and given the code name F7-38-YS.

The first act of asexual reproduction of Flare was accomplished when vegetative cuttings were taken from the initial selection in February, 1978 in a controlled environment in West Chicago, Ill. by a technician working under formulations established and supervised by Leonard H. Shoesmith. Horticultural examination of selected units initiated in March, 1978 has demonstrated that the combination of characteristics as herein disclosed for Flare are firmly fixed and are retained through successive generations of asexual reproduction.

Flare has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Flare, which in combination distinguish this Chrysanthemum as a new and distinct cultivar:

1. Flat capitulum form.
2. Single capitulum type.
3. Bronze-gold flower color.
4. Eight (8) week response.
5. Dwarf habit, extending 10–15 cm. in height from edge of pot when properly grown.

6. Ability to be grown year around in 9 cm. pots in most areas, and requiriIng little B-9 treatment.

Of the many commercial cutivars known to the present inventor, the most similar in comparison to Flare is the cultivar Brightlight, disclosed in U.S. plant patent application Ser. No. 603,840, filed Apr. 25, 1984. In comparison to Brightlight, Flare has a more bronze-gold flower color while the flowers of Brightlight are very yellow. Flare is more compact than Brightlight and easier to grow in 9 cm. pots. The flower type, form and response of Flare are similar to those same characteristics of Brightlight.

The accompanying photographic drawing shows typical inflorescense characteristics of Flare, with colors being as nearly true as possible with illustrations of this type. The photograph is in black and white, with a single flower being colored to accurately depict true flower color.

In the following description color references are made to The Royal Horticultural Society Colour Chart. The color values were determined at approximately 11:00 a.m. on Jan. 17, 1985 under natural and fluorescent light at Bradenton, Fla.

Classification:

*Botanical.*—Chrysanthemum morifolium, Ramat., CV Flare.

*Comercial.*—Daisy spray, four (4) inch pot.

I. INFLORESCENCE

A. Capitulum:

*Form.*—Flat.

*Type.*—Daisy.

*Diameter across face.*—4–6 cm.

B. Corolla of Ray Florets:

*Color (general tonality from a distance of three meters).*—Butterscotch Yellow.

*Color (under surface).*—14 C.

*Color (top surface).*—14 A.

C. Corolla of disc florets:

*Color (Mature).*—Golden yellow.

*Color (immature).*—Lime green.

D. Reproductive organs:

*Androecium.*—Present in disc florets only; numerous.

*Gynoecium.*—Present in both ray and disc florets; numerous.

II. PLANT

A. General appearance:

*Height.*—10–15 cm. above edge of pot when properly grown.

B. Foliage:

*Color* (*under surface*).—147 B.

*Color* (*top surface*).—147 A.

*Shape.*—Ovate and deeply lobed.

It is claimed:

1. A new and distinct cultivar of Chrysanthemum named Flare as described and illustrated, and particularly characterized by its dwarf habit; flat capitulum form and single capitulum type; bronze-gold ray florets; eight week response and by its ability to be grown year around in 9 cm. pots with little growth regulation.

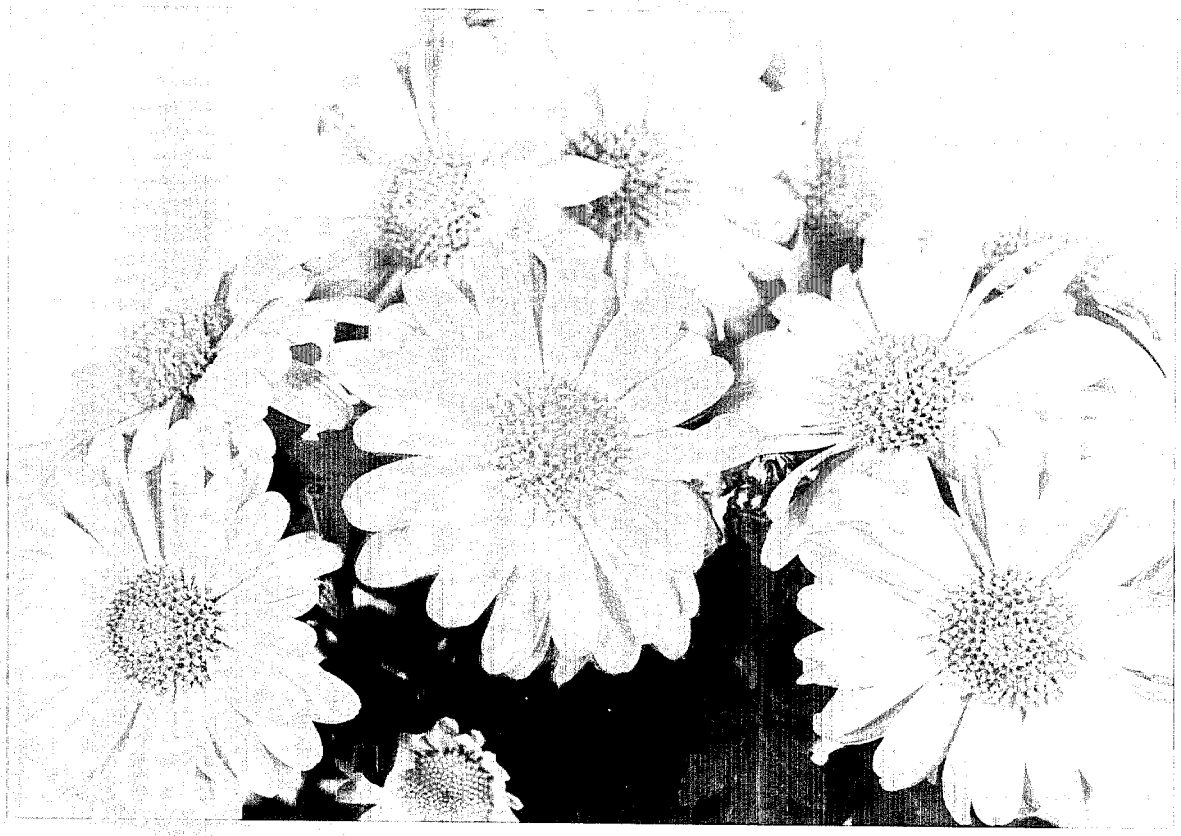

* * * * *